United States Patent
Sklar

(10) Patent No.: US 7,235,074 B1
(45) Date of Patent: Jun. 26, 2007

(54) LIGAMENT SHIM

(76) Inventor: Joseph H. Sklar, 210 Park Dr., Longmeadow, MA (US) 01106

( * ) Notice: Subject to any disclaimer, the term of this patent is extended or adjusted under 35 U.S.C. 154(b) by 0 days.

(21) Appl. No.: 09/612,055

(22) Filed: Jul. 7, 2000

Related U.S. Application Data

(60) Provisional application No. 60/143,241, filed on Jul. 9, 1999.

(51) Int. Cl.
*A61B 17/56* (2006.01)
(52) U.S. Cl. .......................... 606/53; 606/72
(58) Field of Classification Search ............... 606/53, 606/72, 232; 623/13.14, 13.11, 13.12
See application file for complete search history.

(56) References Cited

U.S. PATENT DOCUMENTS

| | | | |
|---|---|---|---|
| 4,750,492 A * | 6/1988 | Jacobs | 606/230 |
| 5,632,748 A * | 5/1997 | Beck, Jr. et al. | 606/89 |
| 5,683,418 A * | 11/1997 | Luscombe et al. | 606/232 |
| 5,876,455 A * | 3/1999 | Harwin | 623/16 |
| 5,899,938 A | 5/1999 | Sklar et al. | |
| 5,931,869 A * | 8/1999 | Boucher et al. | 623/13 |
| 5,961,520 A | 10/1999 | Beck et al. | |
| 6,001,100 A * | 12/1999 | Sherman et al. | 606/72 |
| 6,027,089 A * | 2/2000 | Maharg et al. | 248/220.21 |
| 6,267,767 B1 | 7/2001 | Strobel et al. | |
| 6,355,066 B1 * | 3/2002 | Kim | 623/13.14 |

FOREIGN PATENT DOCUMENTS

| | | |
|---|---|---|
| EP | 0306018 A | 3/1989 |
| WO | WO 98/22047 | 5/1998 |
| WO | WO 98/232229 A1 * | 6/1998 |
| WO | WO 00/18332 | 4/2000 |

\* cited by examiner

*Primary Examiner*—Melba Bumgarner
(74) *Attorney, Agent, or Firm*—St. Onge Steward Johnston & Reens LLC

(57) ABSTRACT

A shim for placement in a bone tunnel during ligament reconstruction.

9 Claims, 21 Drawing Sheets

OPTIONAL: ROUND SURFACES NEAR MOUTH OF BONE TUNNEL, TO PROVIDE GENTLE BEARING SURFACES FOR LIGAMENT

OPTIONAL: ROUND SURFACES NEAR MOUTH OF BONE TUNNEL, TO PROVIDE GENTLE BEARING SURFACES FOR LIGAMENT

US 7,235,074 B1

LIGAMENT SHIM

This patent application claims benefit of pending prior U.S. Provisional Patent Application Ser. No. 60/143,241, filed Jul. 9, 1999 by Joseph H. Sklar for LIGAMENT SHIM, which patent application is incorporated herein by reference.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause pain.

Various procedures have been developed to repair or replace a damaged ligament. The specific procedures used depend on the particular ligament which is to be restored and the extent of the damage.

One ligament which is frequently damaged as the result of injury and/or accident is the anterior cruciate ligament (ACL). The ACL 2 extends between the top of the tibia 4 and the bottom of the femur 6 (FIG. 1). A damaged ACL can cause instability of the knee joint and cause substantial pain and arthritis.

Numerous procedures have been developed to restore the ACL through a graft ligament replacement. In general, these ACL 2 replacement procedures (FIG. 2) involve drilling a bone tunnel 8 through the tibia 4 and up into the femur 6. Then a graft ligament 10, consisting of a harvested or artificial ligament or tendon(s), is passed through the tibial tunnel 12, across the interior of the joint, and up into the femoral tunnel 14. Then a distal portion of the graft ligament is secured in the femoral tunnel 14 and a proximal portion of the graft ligament is secured in the tibial tunnel 12.

There are currently several different ways to secure a graft portion in a bone tunnel. One way is to use an interference screw 16 (FIG. 2) to aggressively wedge the graft ligament against the side wall of the bone tunnel. Another way is to suspend the graft ligament in the bone tunnel with a suture 18 (FIG. 3) or a cross-pin 20 (FIG. 4). Still another way is to pass the graft ligament completely through the bone tunnel and affix the ligament to the outside of the bone with a screw and washer arrangement 22 (FIG. 2) or a staple (not shown).

Depending on the fixation device and its manner of use, some fixation will occur at the portion of the bone tunnel nearest to the interior of the joint, and some fixation will occur intermediate the bone tunnel or adjacent to the portion of the bone tunnel farthest from the interior of the joint. For example, an interference screw 16 set into the femur 6 will typically be positioned substantially adjacent to the interior of the joint 26 (FIG. 5); however, an interference screw 16 set into the tibia 4 will frequently be positioned relatively far from the interior of the joint 26 (FIG. 6). On the other hand, suture 18 (FIG. 3) and cross-pin 20 (FIG. 4) suspensions will typically effect securing intermediate the length of the bone tunnel or at the far end of the bone tunnel, and screw and washer fixations 22 (FIG. 2) will typically effect securing relatively far from the interior of the joint 26.

It has been observed that whenever the graft ligament is secured remote from the interior of the joint 26 (i.e., in the middle of the bone tunnel or adjacent to an outer surface of the bone), the graft ligament 10 will be relatively unsupported at the point where the ligament 10 passes from the bone tunnel into the interior of the joint. As a result, as the knee flexes back and forth through its natural range of motion (FIG. 7), the graft ligament moves about within the mouth 28 of the bone tunnel, rubbing against the walls of the bone tunnel. Over time, this can cause damage to the graft ligament and the wear down the mouth 28 of the bone tunnel, both to the serious detriment of the patient. It can also result in enlargement of the entire tunnel diameter, e.g., as shown at 30. Less than a tight fit may result in incursion of synovial fluid into the tunnel, which is hypothesized to contribute to the tunnel-widening phenomenon.

DETAILED DESCRIPTION OF THE PREFERRED EMBODIMENTS

Figure 1:
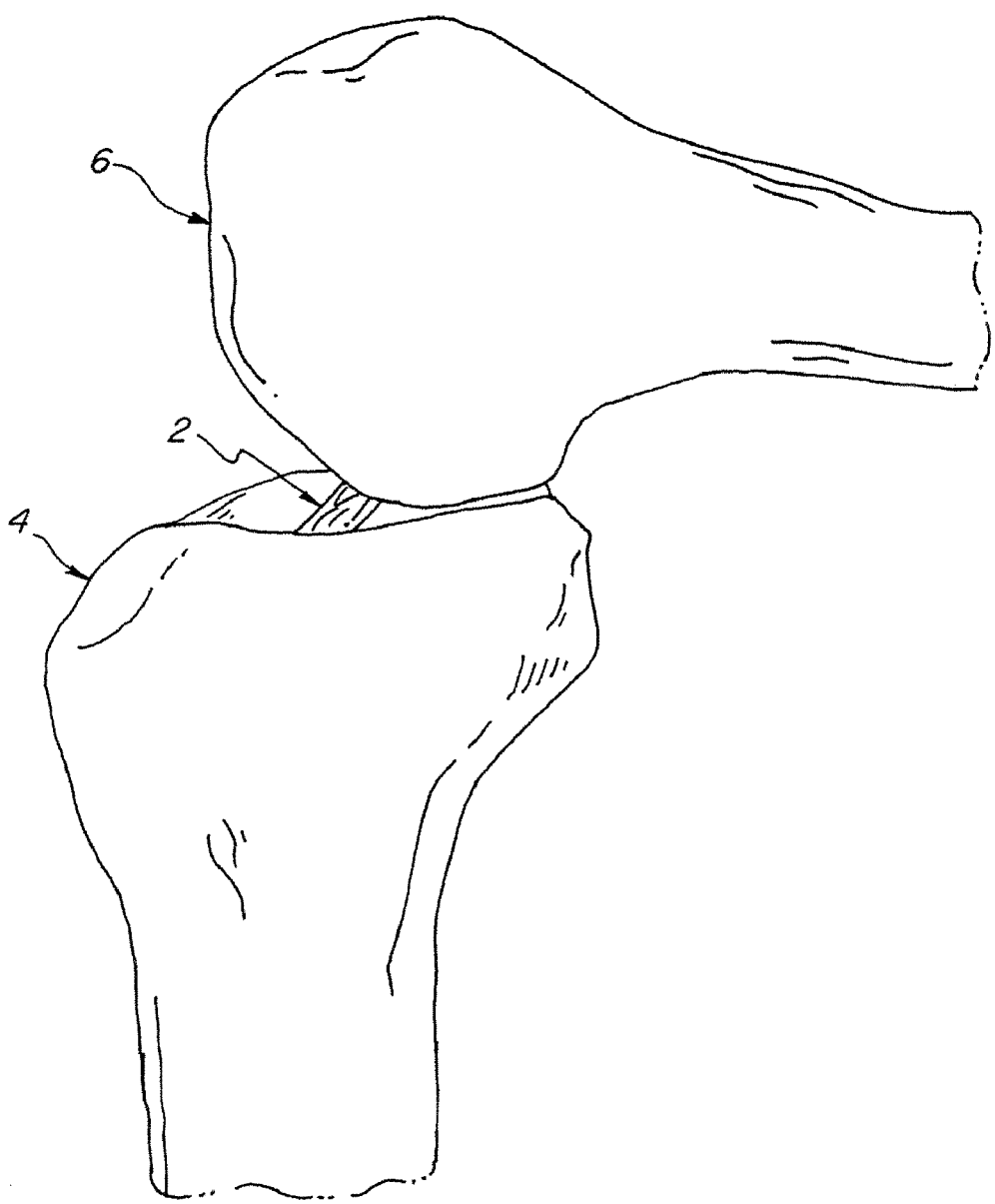
FIG. 1 is a schematic illustration of an ACL extending between the top of the tibia and the bottom of the femur.
Figure 2:
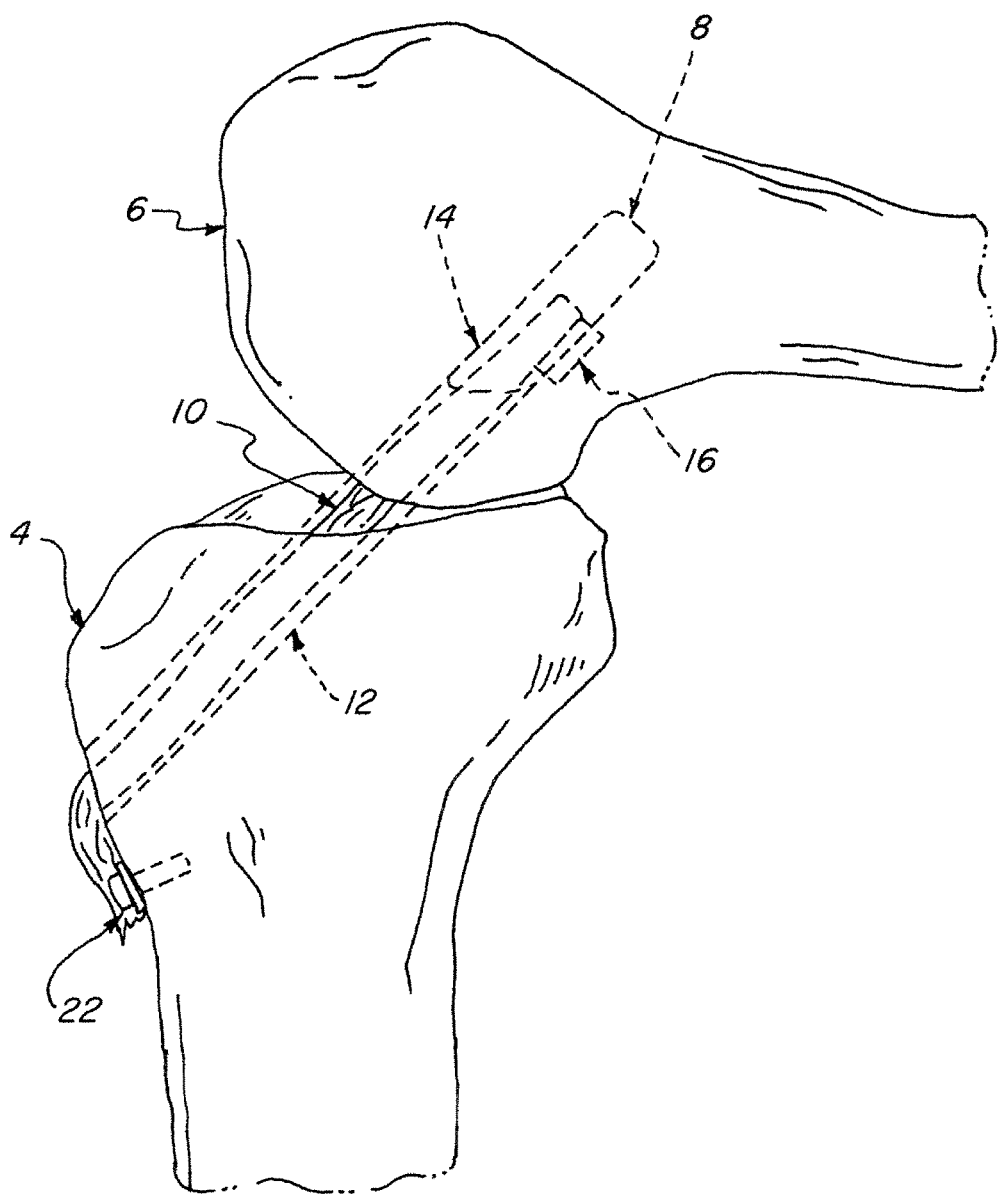
FIG. 2 is a schematic illustration of an ACL replacement procedure using an interference screw to wedge a graft ligament against the side wall of a bone tunnel.
Figure 3:
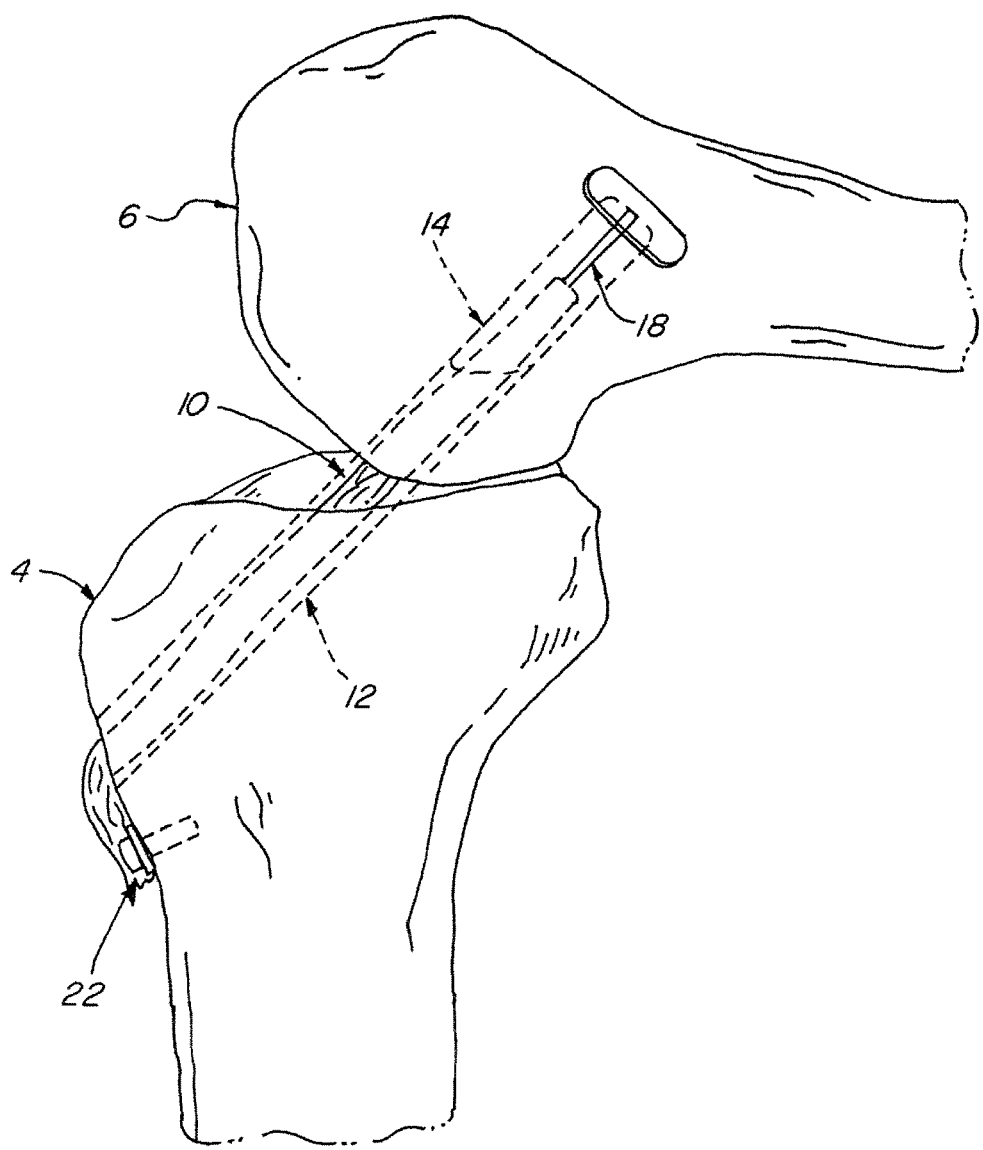
FIG. 3 is a schematic illustration of an ACL replacement procedure using a suture to suspend a graft ligament in a bone tunnel.
Figure 4:
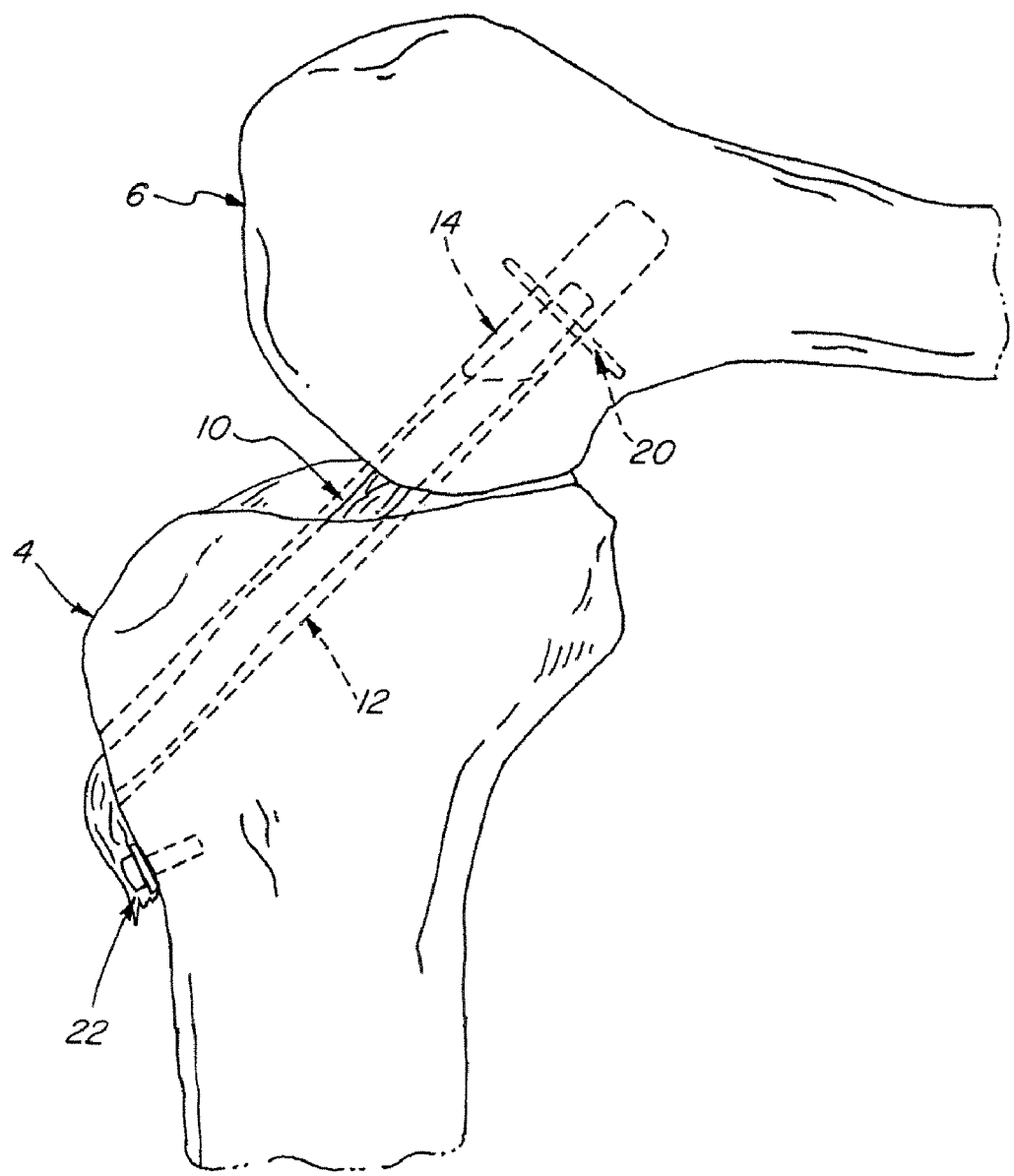
FIG. 4 is a schematic illustration of an ACL replacement procedure using a cross-pin to suspend a graft ligament in a bone tunnel.
Figure 5:
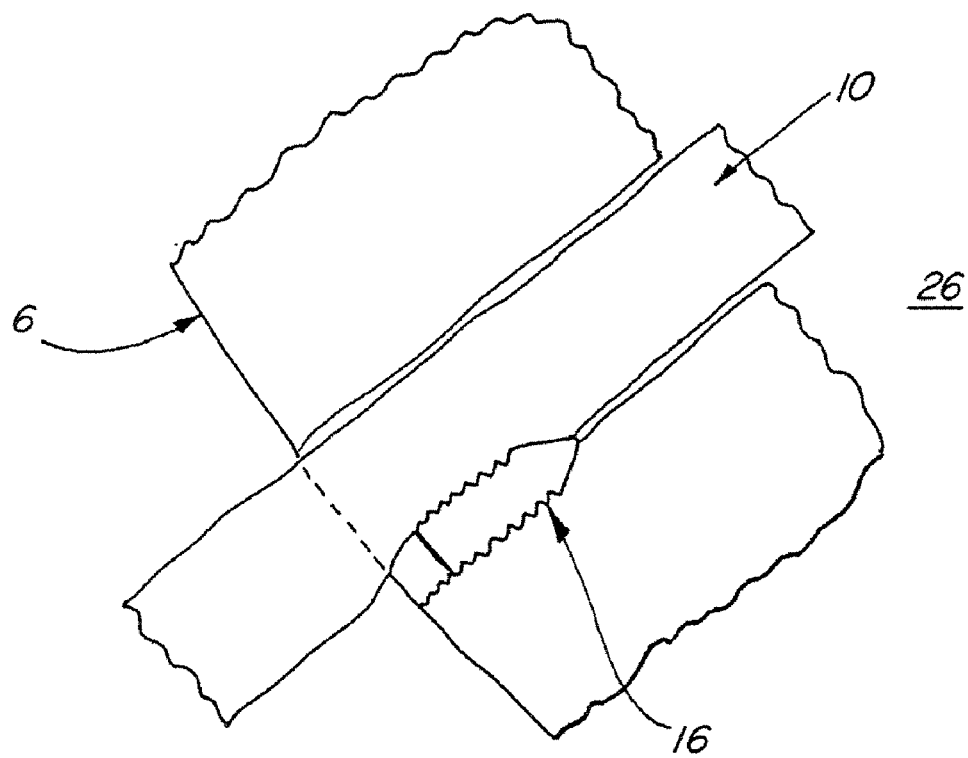
FIG. 5 is a schematic illustration of an interference screw set into a femur and positioned substantially adjacent to the interior of the joint.
Figure 6:
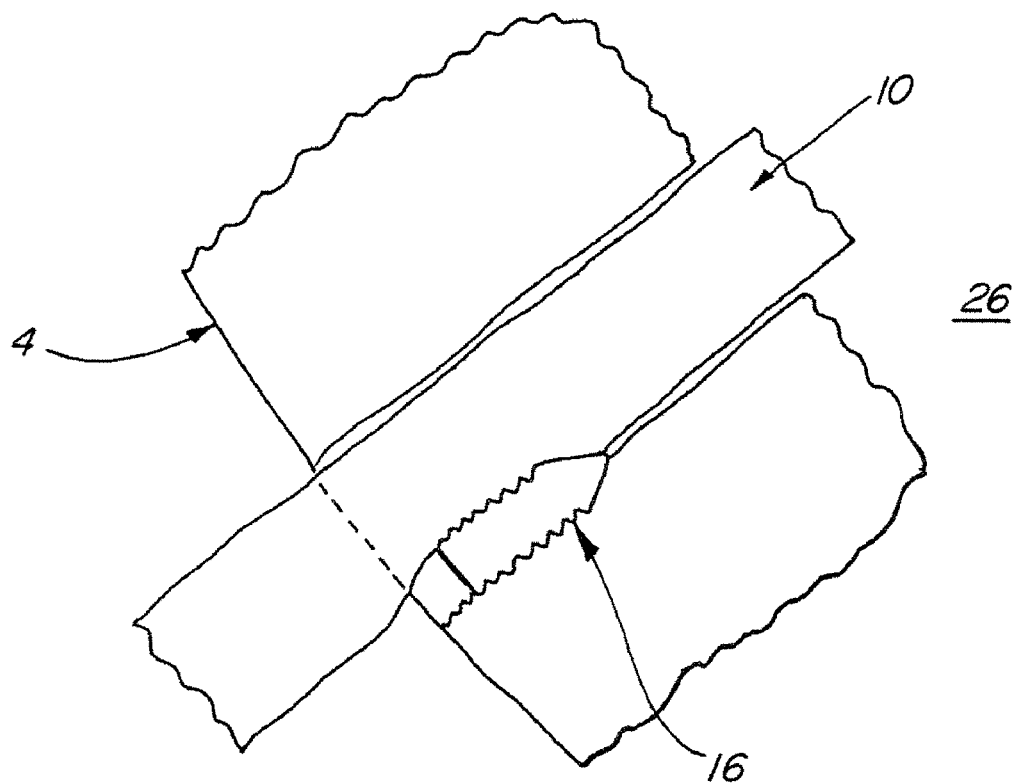
FIG. 6 is a schematic illustration of an interference screw set into a tibia and positioned relatively far from the interior of the joint.
Figure 7:
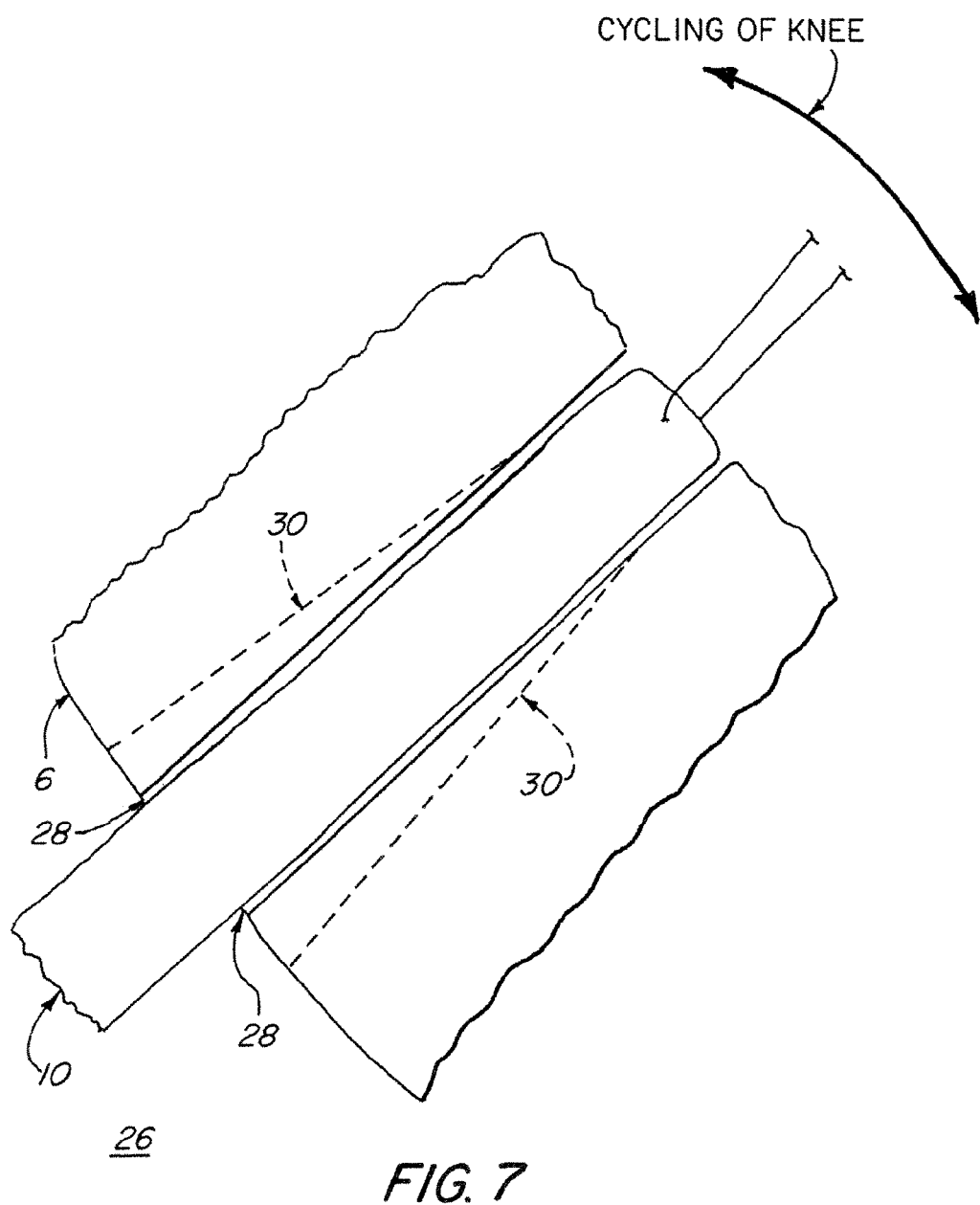
FIG. 7 is a schematic illustration of a graft ligament within the mouth of a bone tunnel, the bone tunnel having an enlarged bone tunnel diameter from the graft ligament moving about within the mouth of the bone tunnel.
Figure 8:
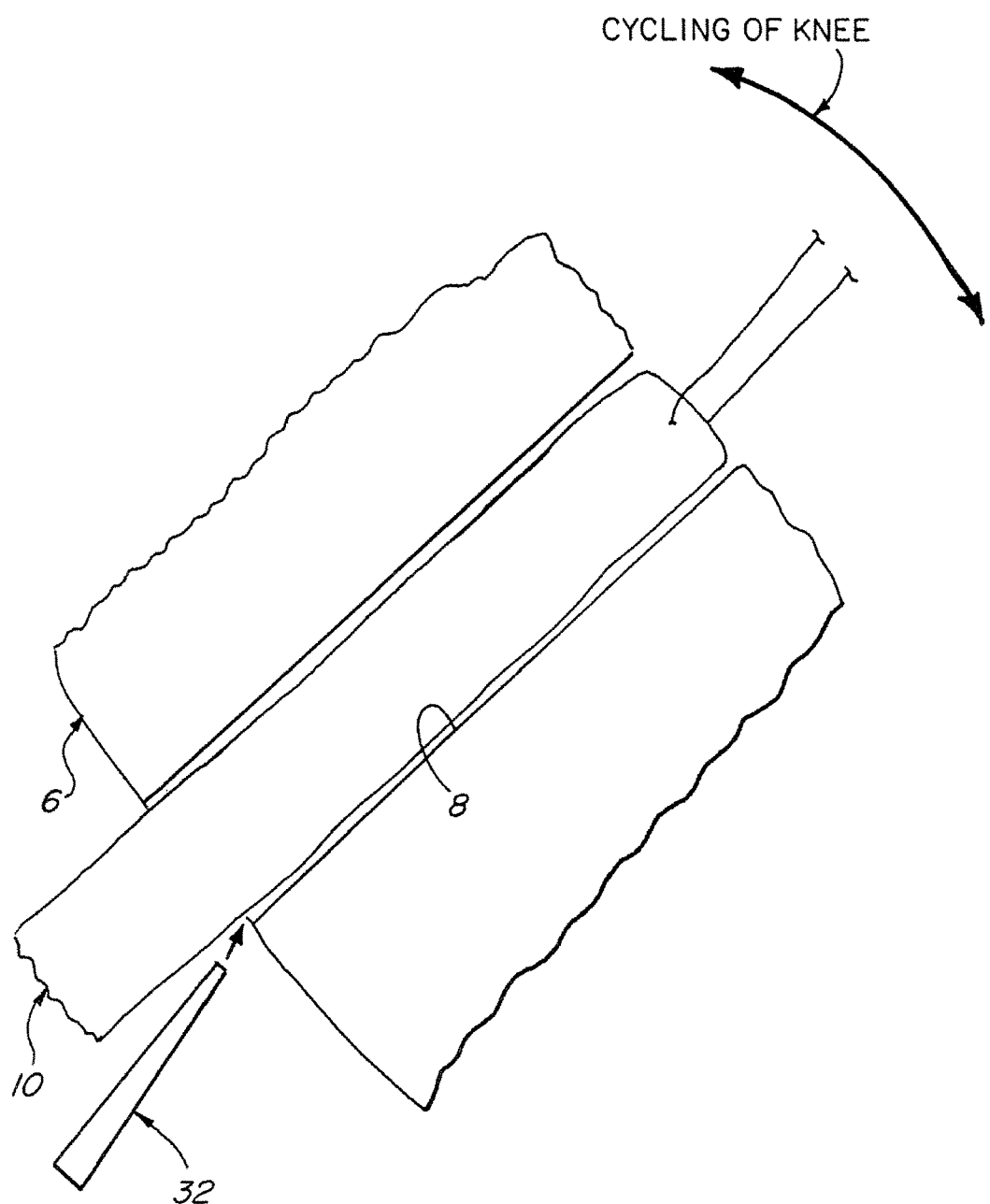
FIG. 8 is a schematic illustration of a shim provided for insertion into the mouth of a bone tunnel.

The solution to this problem is to provide a shim 32 for insertion into the mouth 28 of the bone tunnel (FIG. 8). The shim 32 is formed and sized so as to take up additional space present at the mouth 28 of the bone tunnel and, at the same time, to urge the ligament against the opposing side walls of the bone tunnel. By taking up additional space at the mouth of the bone tunnel, the aforementioned windshield wiper effect can be effectively eliminated. In addition, the entrance to the bone tunnel will be better sealed against migration of synovial fluid out of the joint and into the bone tunnel. This can be important, since incursion of synovial fluid into the bone tunnel is believed to be deleterious to the ligament reconstruction and to contribute to tunnel widening. At the same time, by urging the graft ligament 10 against the opposing side walls of the bone tunnel 8, osseo-integration between the graft ligament and the host bone will be enhanced. If desired, the shim 32 can be sized and positioned so as to force the ligament 10 against the opposing side walls of the bone tunnel 8 with substantial force so as to enhance attachment of the graft ligament 10 to the bone. However, it should also be appreciated that it is not necessary for the ligament shim 32 to force the ligament against the opposing side walls of the bone tunnel with any great force, since the primary purpose of the shim is simply to occupy excess bone tunnel space, not to compressively secure the ligament to the bone. In other words, the primary purpose of the ligament shim is to form a strategically-placed extension of the bone tunnel wall, rather than to replace an interference screw.

The ligament shim can take the form of two basic embodiments; a peripheral shim 34 and a centerline shim 36.

Figure 9:
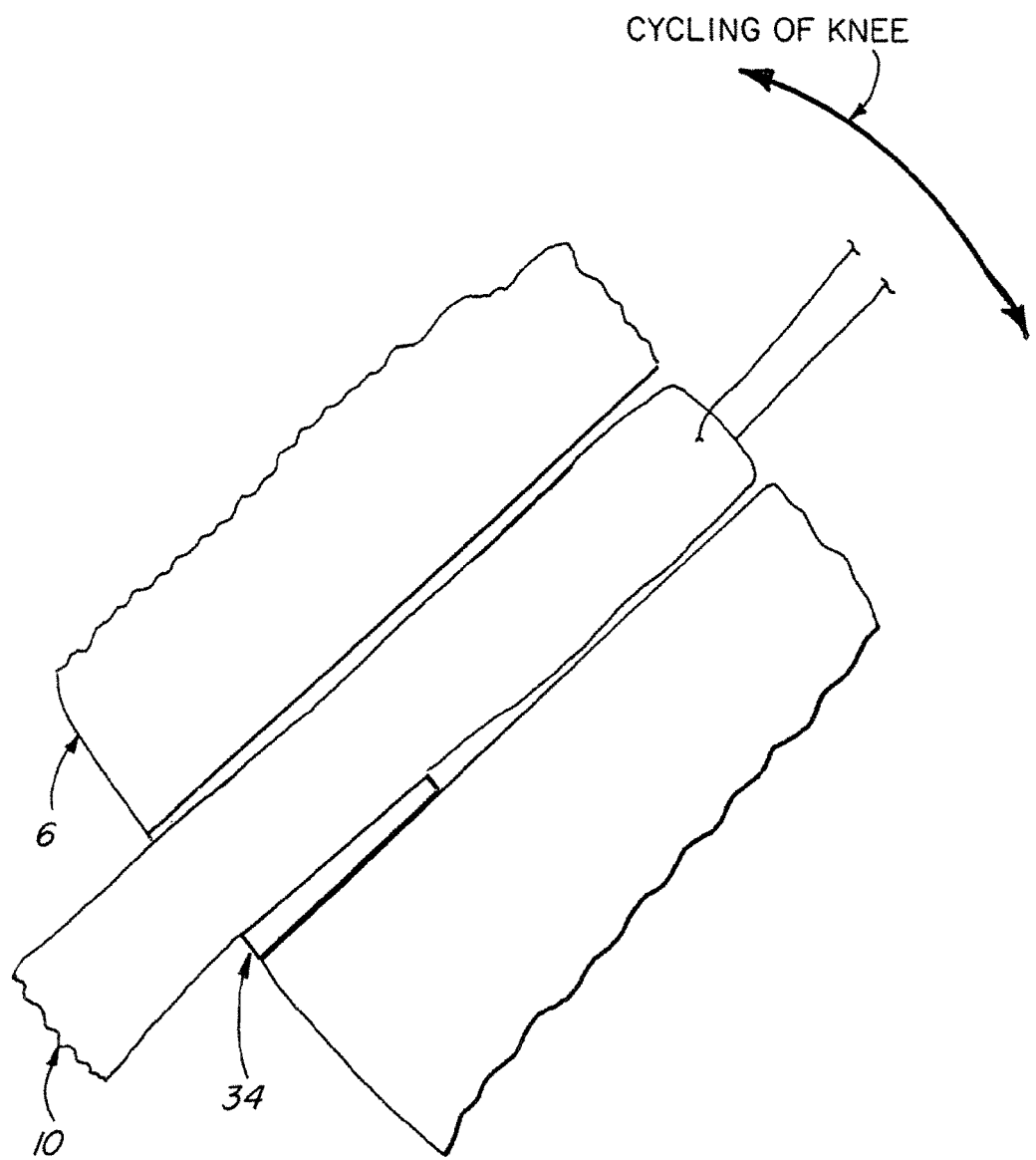
FIG. 9 is a schematic illustration of a peripheral shim adapted to fit between a graft ligament and the wall of a bone tunnel.
Figure 10:
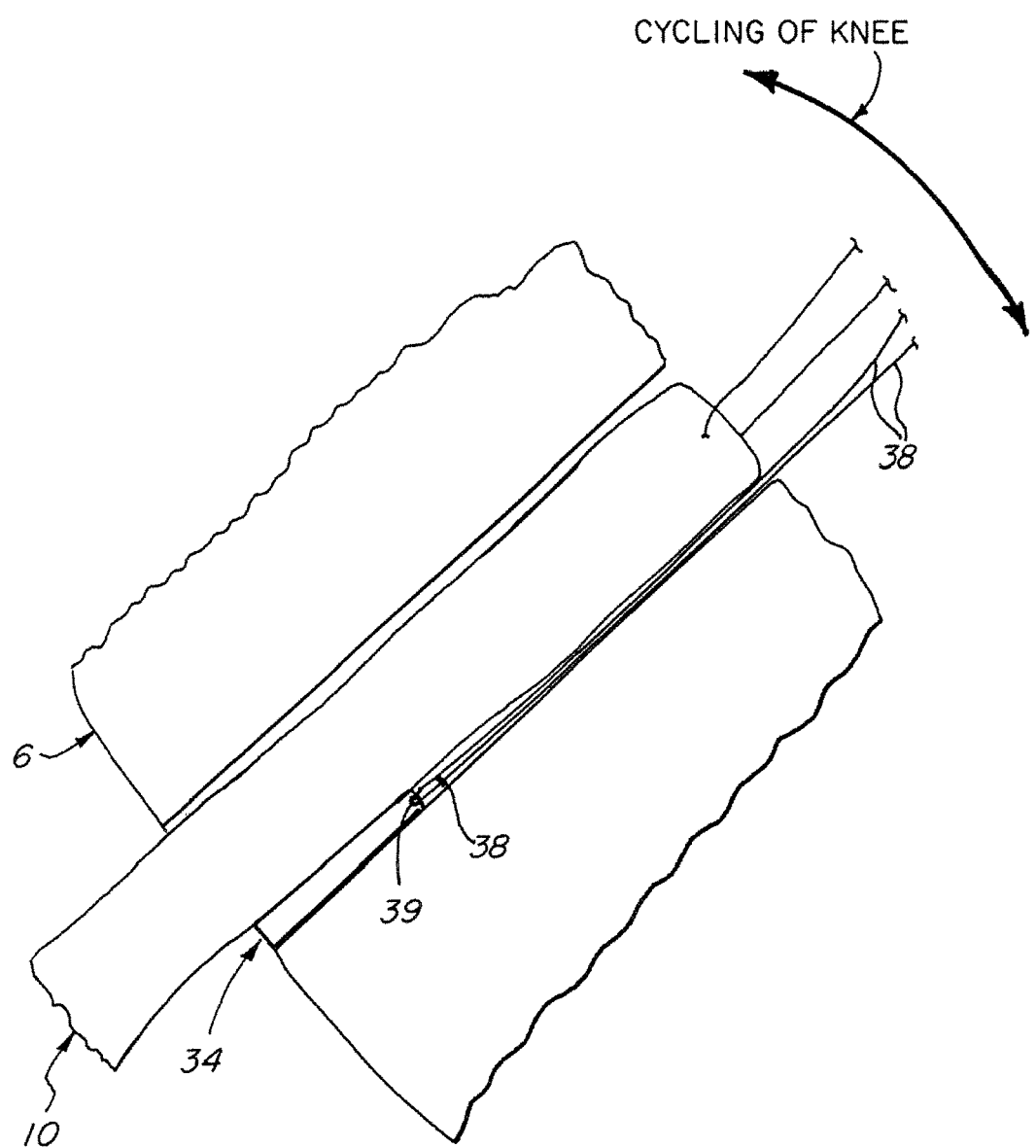
FIG. 10 is a schematic illustration of the peripheral shim suspended by a suture inserted through a shim hole therein.

The peripheral shim 34 is adapted to fit between the graft ligament 10 and a wall of the bone tunnel (FIG. 9). Thus, the shim effectively provides an extension of the bone wall which it lies against, so as to eliminate the windshield wiper effect discussed above. In one form of the invention, the shim 34 is intended to be held in place through a simple friction fit between the wall of the bone tunnel and the graft ligament. If desired, the shim can be tapered (FIGS. 8 and 9) so as to give it a wedge-like configuration and/or the surfaces of the shim can be configured with ribs and/or roughening so as to increase friction with the adjacent anatomy. In another form of the invention, the shim can be suspended by a suture 38 which passes through a shim hole 39 (FIG. 10). Preferably, a shim has at least its outer surface in the shape of an arc (FIG. 11), so that it can conform to the round bone tunnel wall. In one embodiment, the shim has both its inner and outer surfaces in the shape of an arc 42 (FIG. 11A), so that it can conform to both the round bone tunnel wall and the round graft ligament. If desired, more than one shim can be applied about the periphery of the mouth of the bone tunnel. Alternatively, a single shim can be constructed so that it covers a significant portion of the periphery of the bone tunnel wall.

Figure 11:
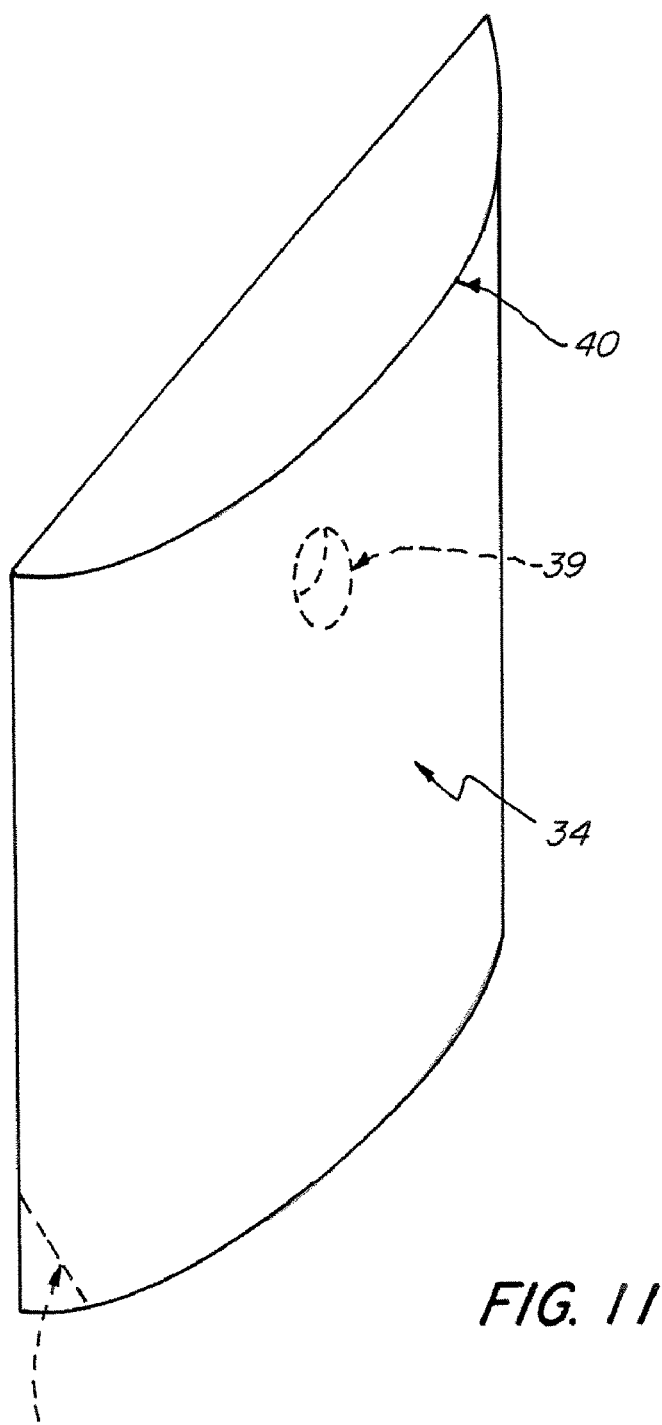
FIG. 11 is a schematic illustration of a shim having an outer surface in the shape of an arc so as to conform to a round bone tunnel wall.
Figure 11A:
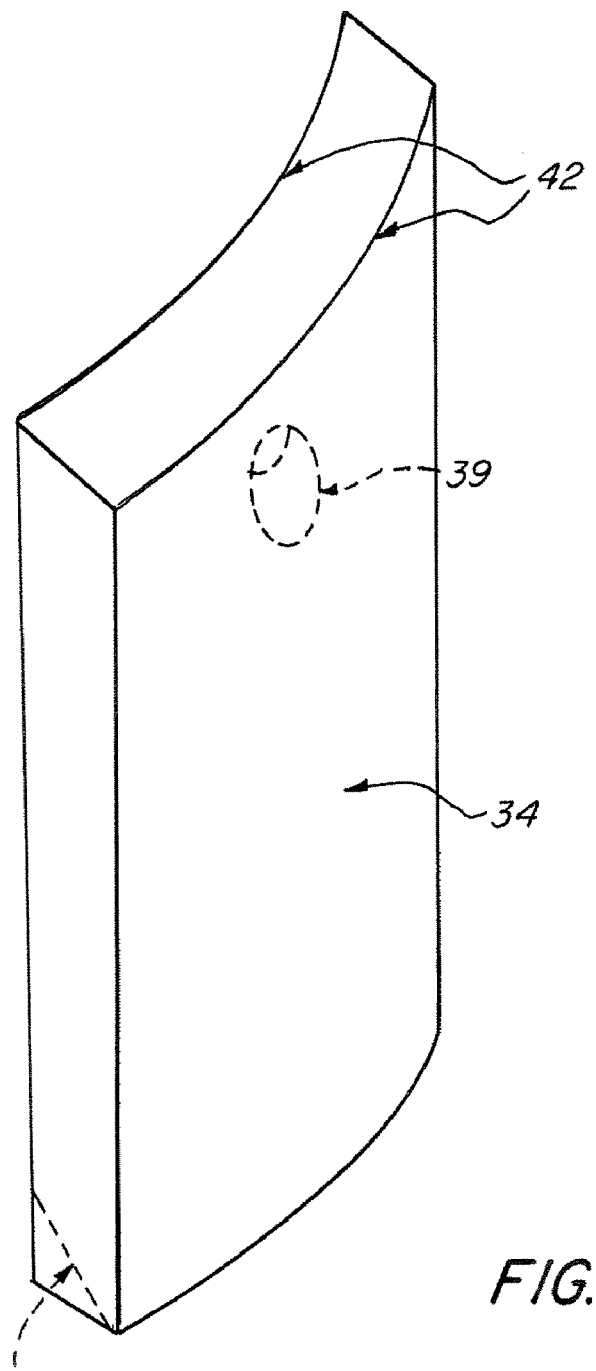
FIG. 11A is a schematic illustration of a shim having both an outer surface and an inner surface in the shape of an arc so as to conform to both the round bone tunnel wall and the round graft ligament.

Still looking at FIGS. 11 and 11A, and in a preferred embodiment of the present invention, there is shown peripheral shim 34 having round surfaces at a proximal end thereof. Peripheral shim 34 may be disposed within a bone tunnel such that these round surfaces provide gentle bearing surfaces for the ligament near the mouth of the bone tunnel.

Figure 12:
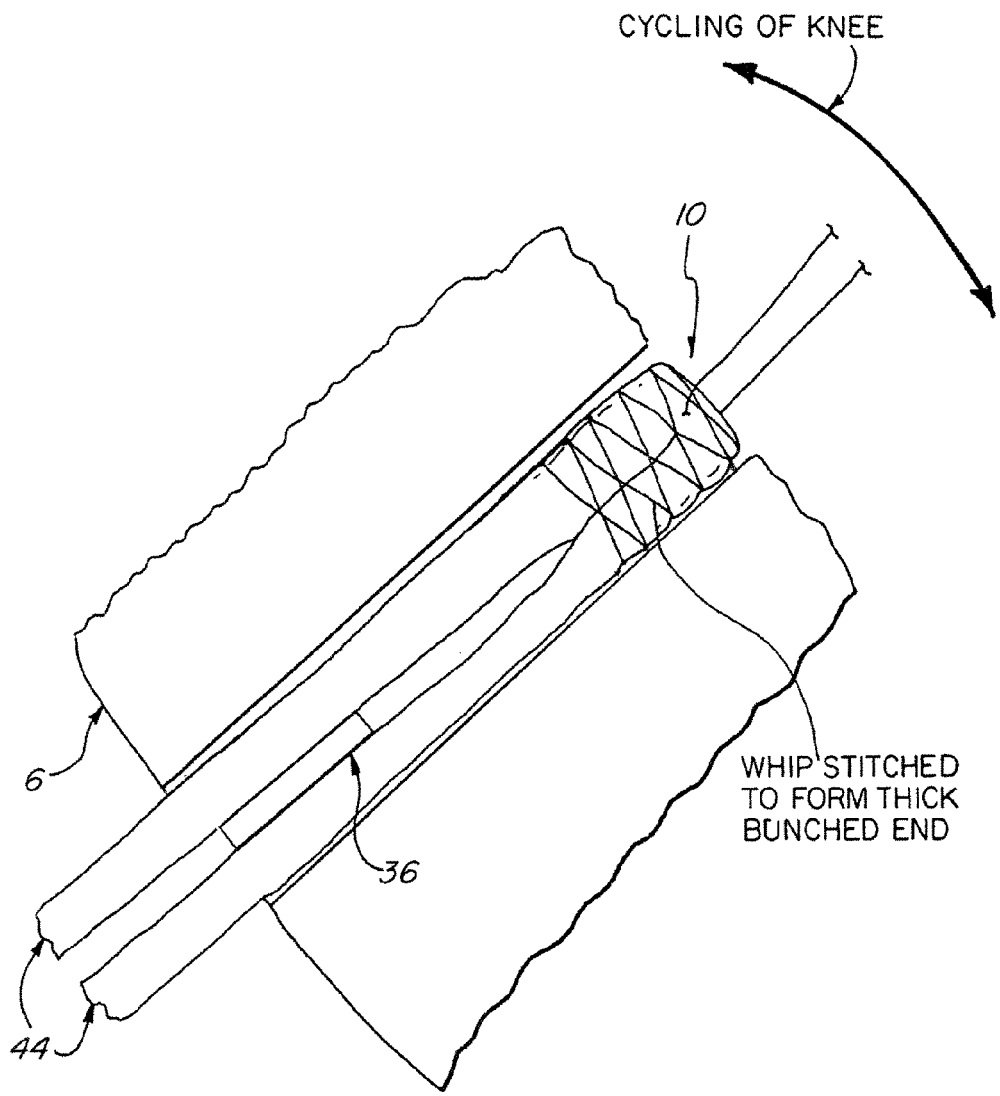
FIG. 12 is a schematic illustration of a centerline shim adapted to fit between two graft ligament strands.
Figure 13:
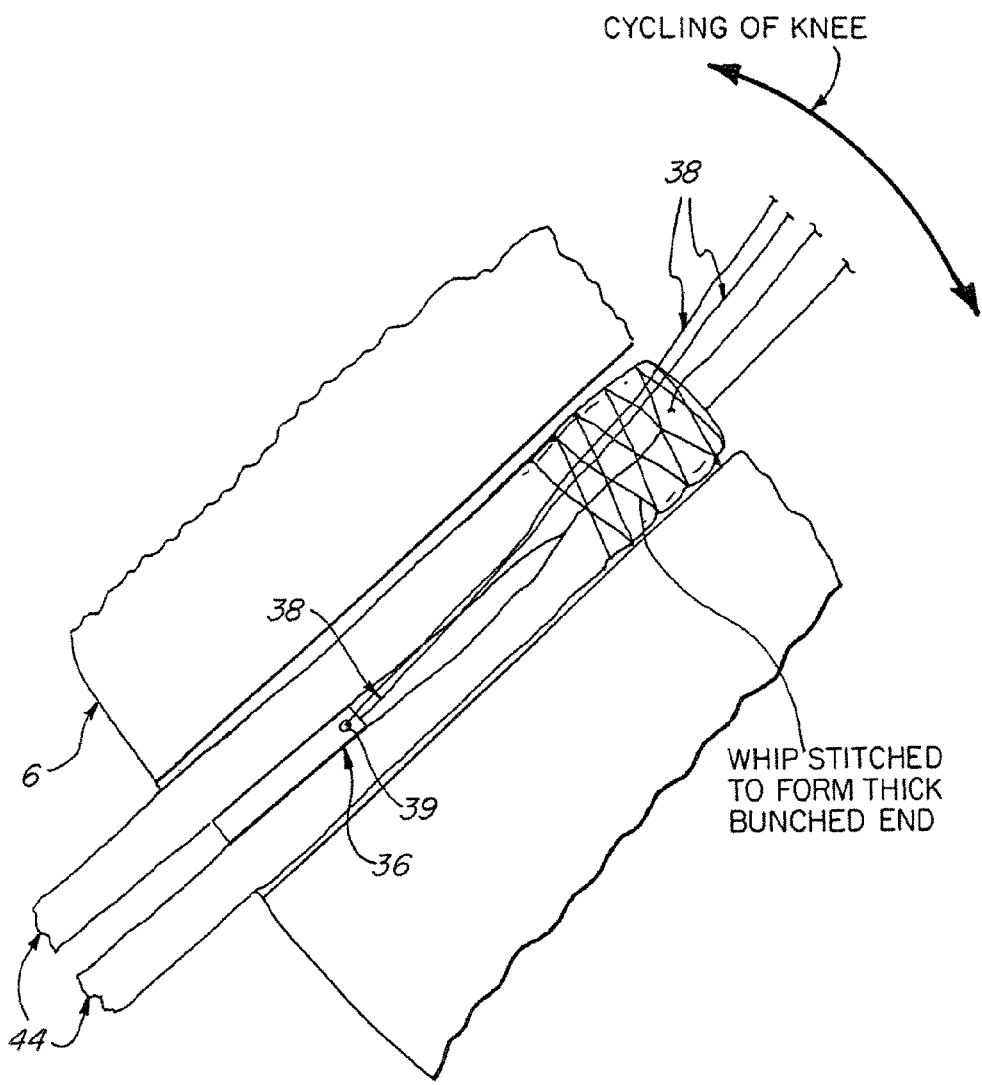
FIG. 13 is a schematic illustration of the peripheral shim suspended by a suture inserted through a shim hole therein.
Figure 14:
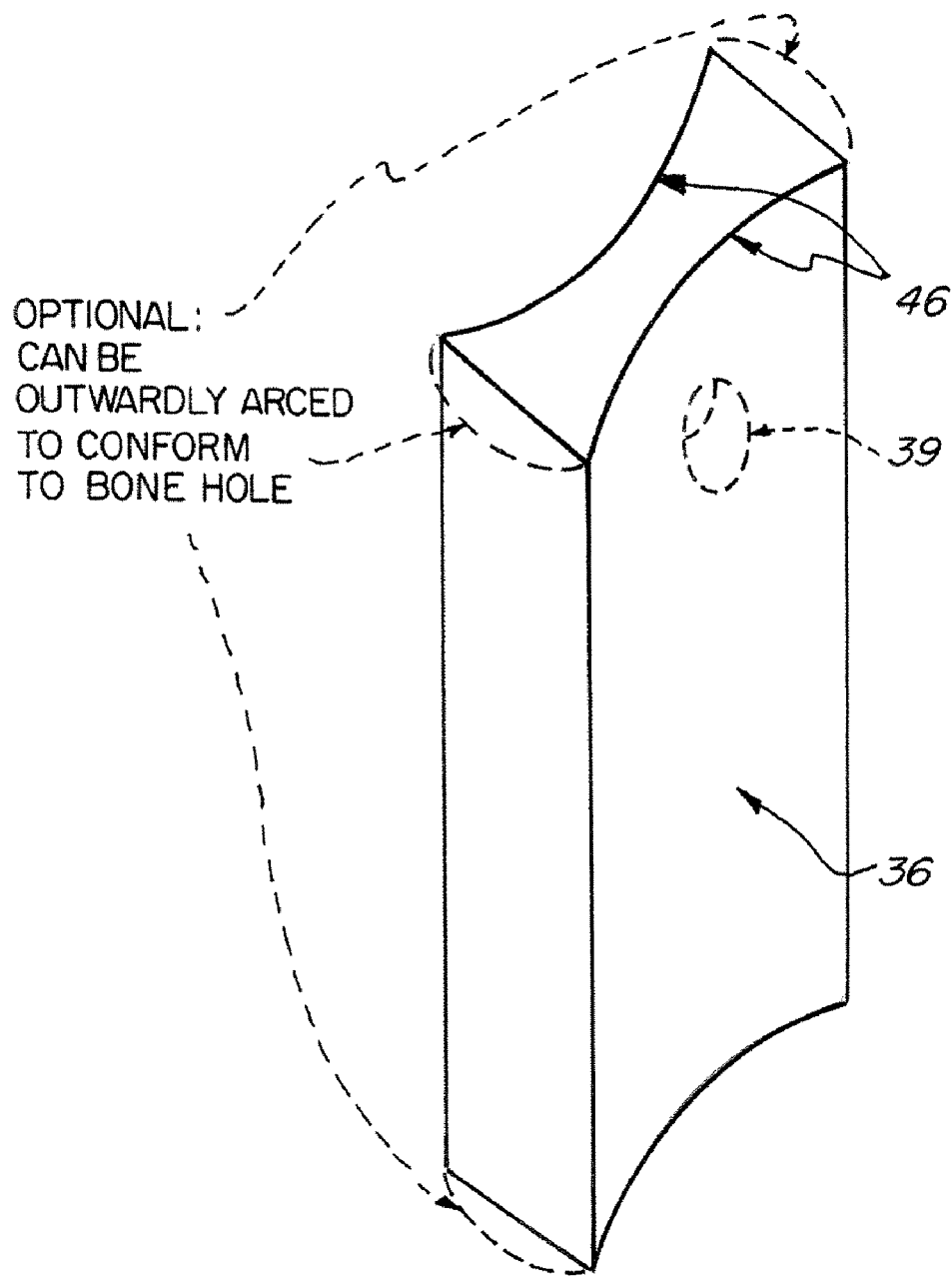
FIG. 14 is a schematic illustration of a centerline shim having two opposing surfaces in the shape of an arc so as to conform to two round graft ligament strands.
Figure 15:
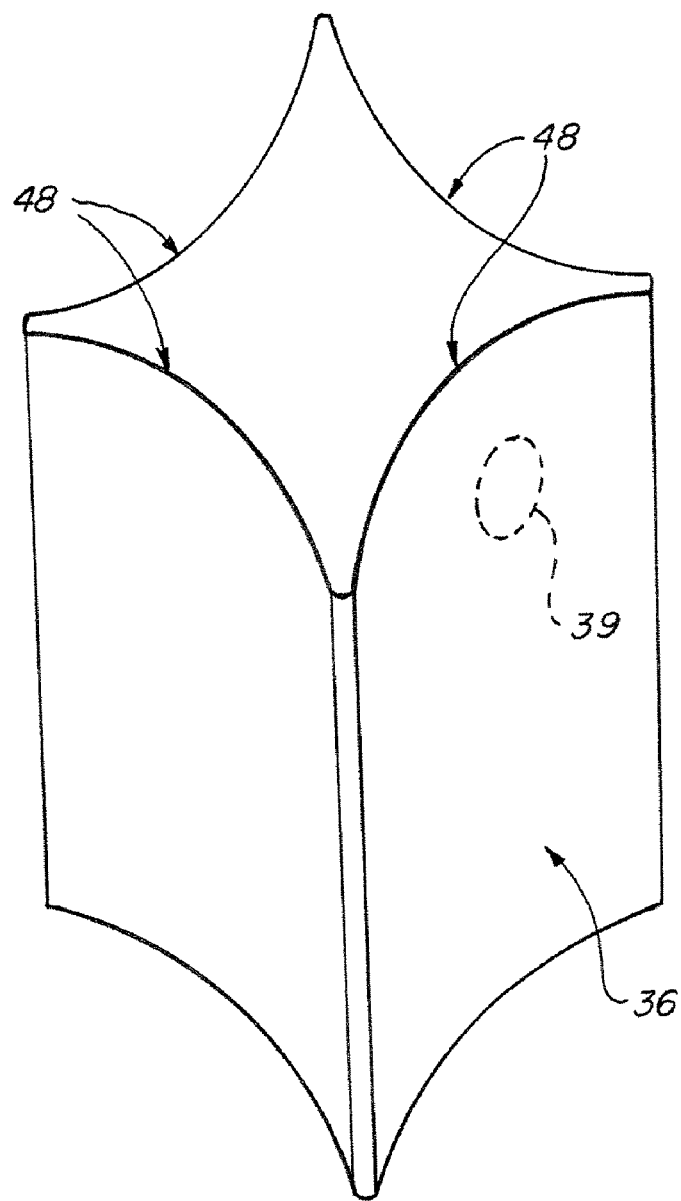
FIG. 15 is a schematic illustration of a centerline shim having a first set of two opposed surfaces in the shape of an arc and a second set of two opposed surfaces in the shape of an arc so as to conform to four round graft ligament strands.
Figure 16:
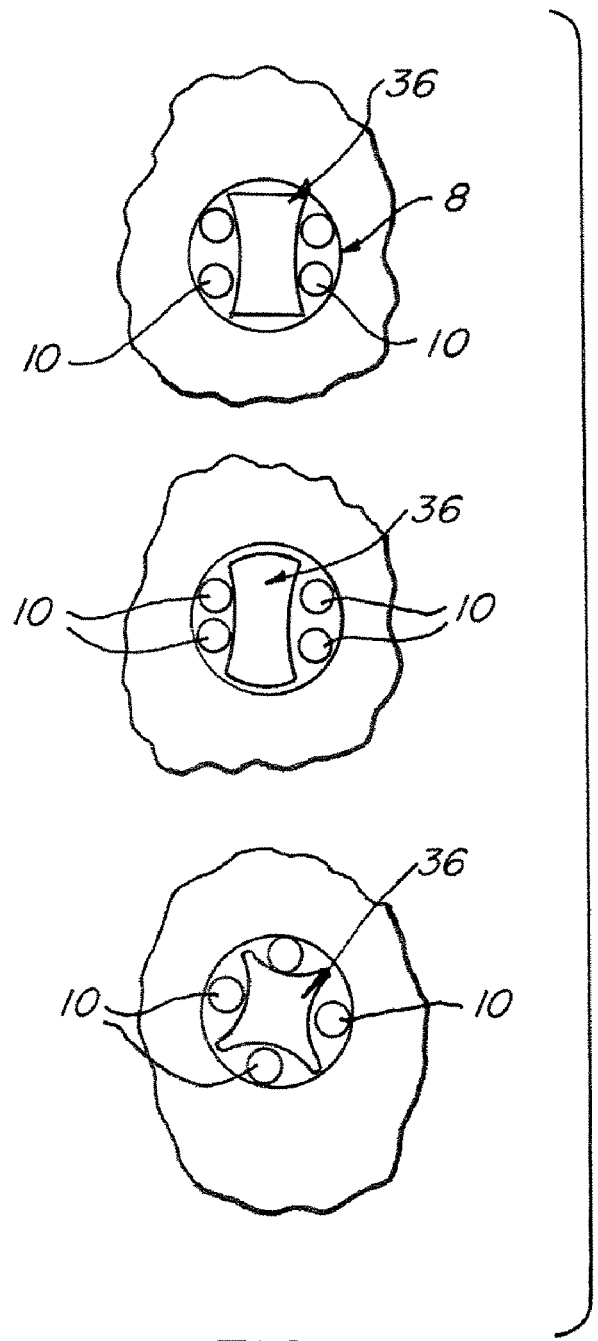
FIG. 16 is a schematic illustration of examplementary implementations of the centerline shim.

In some circumstances, the graft ligament consists of single strand of tissue (FIG. 9). In other circumstances, the graft ligament consists of two or more strands 44 of tissue which extend parallel to one another so as to collectively form the graft ligament 10 (FIG. 12). For example, suture and cross-pin suspensions are typically created by looping a long hamstring graft 44 over a suture loop or cross-pin; in this case, there are two graft ligament strands extending parallel to one another in the bone tunnel. The centerline shim 36 is adapted to fit between two such graft ligament strands 44. The centerline shim 36 can be maintained in place through a simple friction fit between the two ligament strands 44 (FIG. 12). Again, the shim can be tapered along its length so as to give it a wedge-like configuration, and/or the surfaces of the shim can be configured with ribs and/or roughening so as to increase friction with adjacent anatomy. Alternatively, the shim can be suspended by a suture 38 passing through a shim hole 39 (FIG. 13). Preferably, the centerline shim has its two opposing surfaces in the shape of an arc 46, so that the shim can conform to the two round graft ligament strands (FIG. 14). This construction will help keep the centerline shim 36 seated between the ligament strands 44. In some cases, more than two ligament strands 44 might be used in the ligament reconstruction. For example, four ligament strands might be used in the reconstruction. In this case, the shim might comprise four arced surfaces 48 (FIG. 15). Numerous implementations of the centerline shim 36 are contemplated (FIG. 16).

Figure 14A:
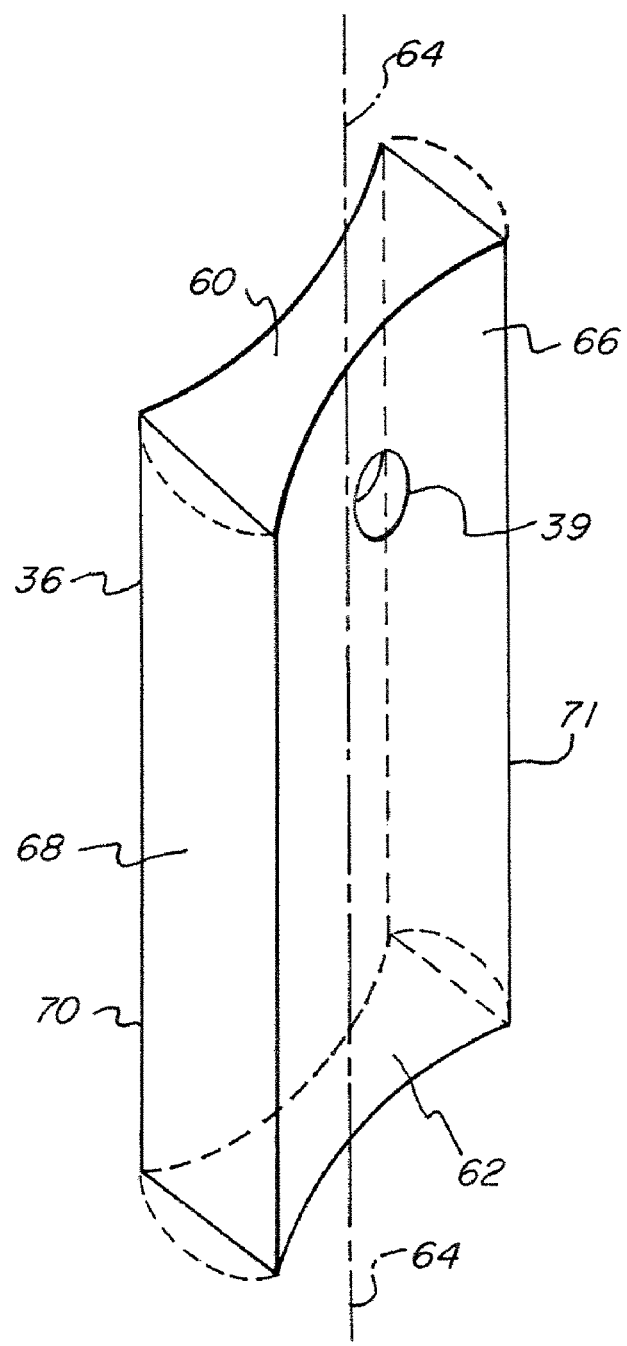
FIG. 14a is a schematic illustration of a centerline shim having two opposing surfaces in the shape of an arc.

FIG. 14a shows one embodiment of the present invention having two opposing surfaces in the shape of an arc. Shim body (36) is shown having a first end (60) and a second end (62), and an axis (64) extending from first end (60) through second end (64). First end (60) and second end (62) are shown as being substantially planar and of substantially the same configuration in plan view, substantially the same size and normal to the axis. First surface (66) and second surface (68) extend from first end (60) to second end (62) substantially parallel to axis (64). First surface (66) and second surface (68) are arc shaped. Shim hole (39) extends from first surface (66) to second surface (68). Apart from shim hole (39), the shim is devoid of any further opening. Wall (70) is also shown extending from first surface (66) to second surface (68). Second wall (71) is also shown extending from first surface (66) to second surface (68) parallel to wall (70). Optionally wall (70) may be rounded. Shim hole (39) extends from a crest of first arc-shaped surface (66) to a mid-arc portion of second arc-shaped surface (68).

Figure 14B:
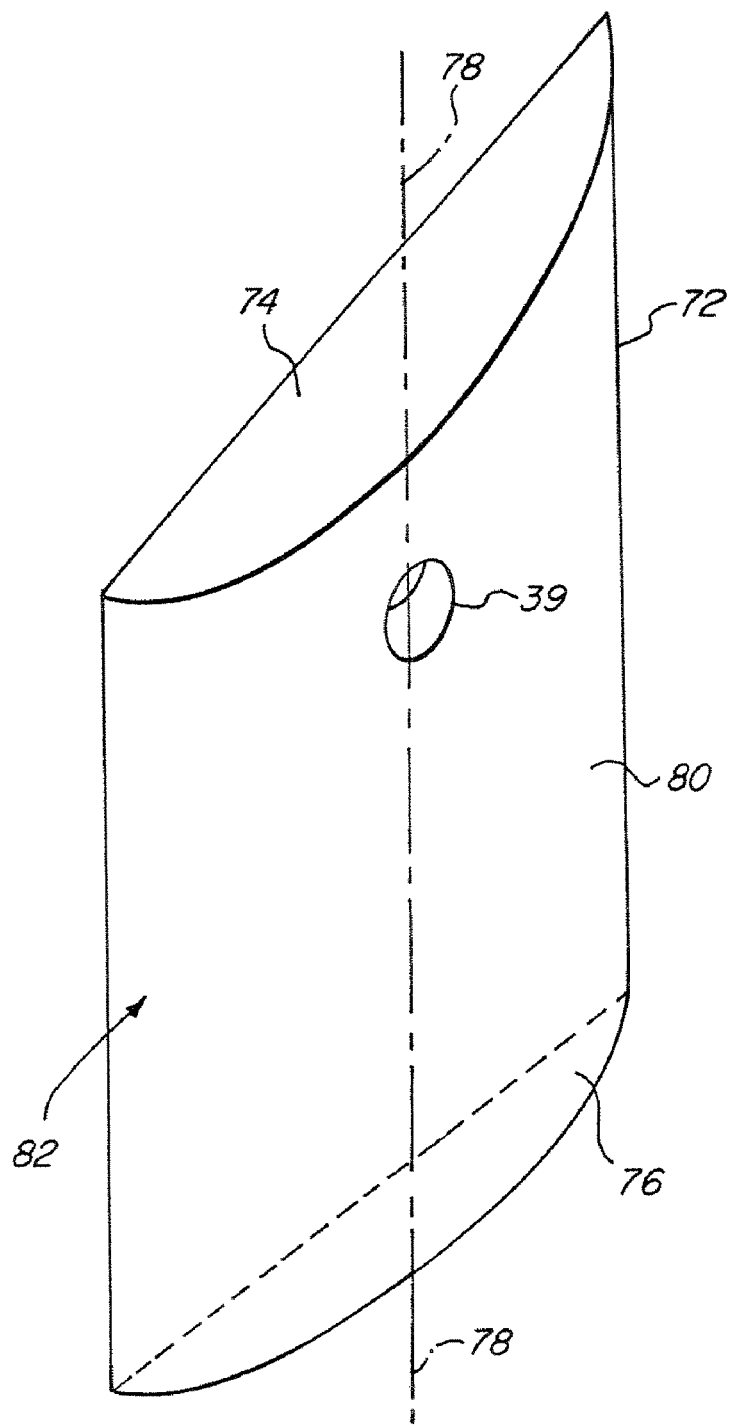
FIG. 14b is a schematic illustration of a shim having an outer surface in the shape of an arc.

FIG. 14b shows another embodiment of the present invention similar to that shown in FIG. 11. Shim body (72) is shown having a first end (74) and a second end (76), and an axis (78) extending from first end (74) through second end (76). First end (74) and second end (76) are shown as being substantially planar. First surface (80) and second surface (82) extend from first end (74) to second end (76) substantially parallel to axis (78). First surface (80) is arc shaped. Second surface (82) is substantially flat. Shim hole (39) extends from first surface (80) to second surface (82). Apart from shim hole (39), the shim is devoid of any further opening.

Both the peripheral shim and the centerline shim also provide a benefit beyond simply curing the aforementioned windshield wiper effect. More specifically, at the same time that the shims take up excess room within the bone tunnel, they also urge the graft ligament into engagement with the walls of the bone tunnel. This urging facilitates osseointegration between the graft ligament and the host bone, thereby improving surgical results.

Figure 17:
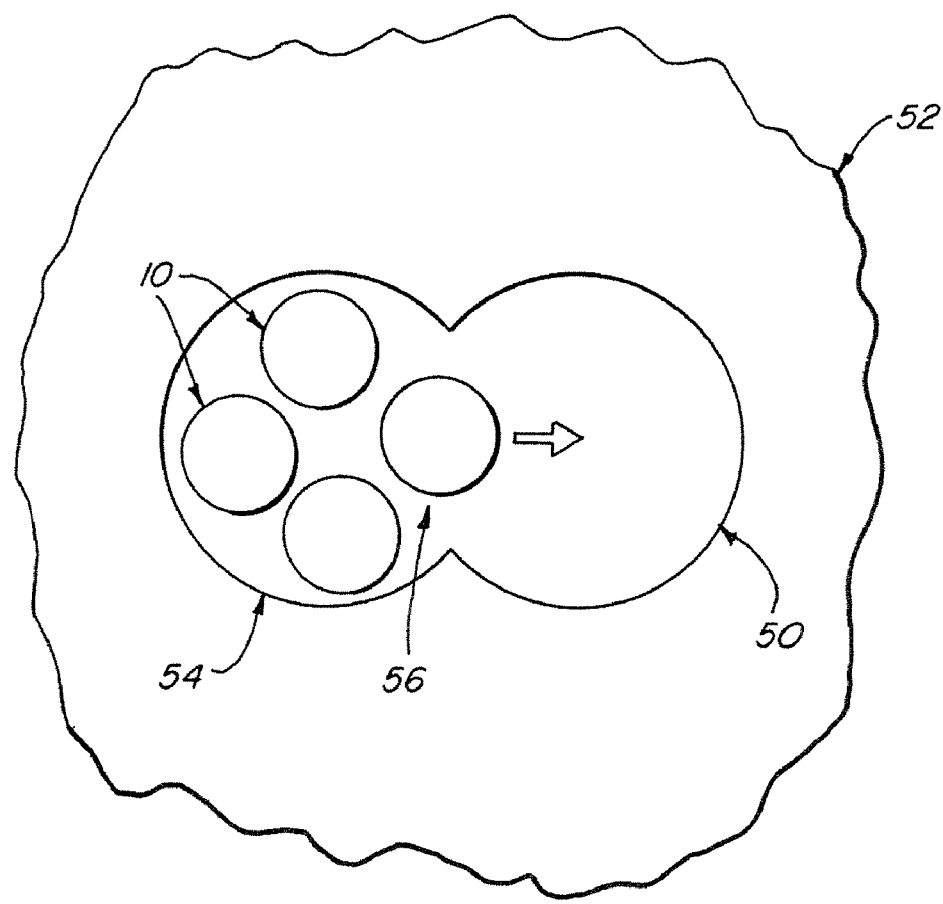
FIG. 17 is a schematic illustration of a new bone tunnel placed close to an old bone tunnel so as to overlap one another, so as to allow a graft ligament strand to fall into the old bone tunnel hole.
Figure 18:
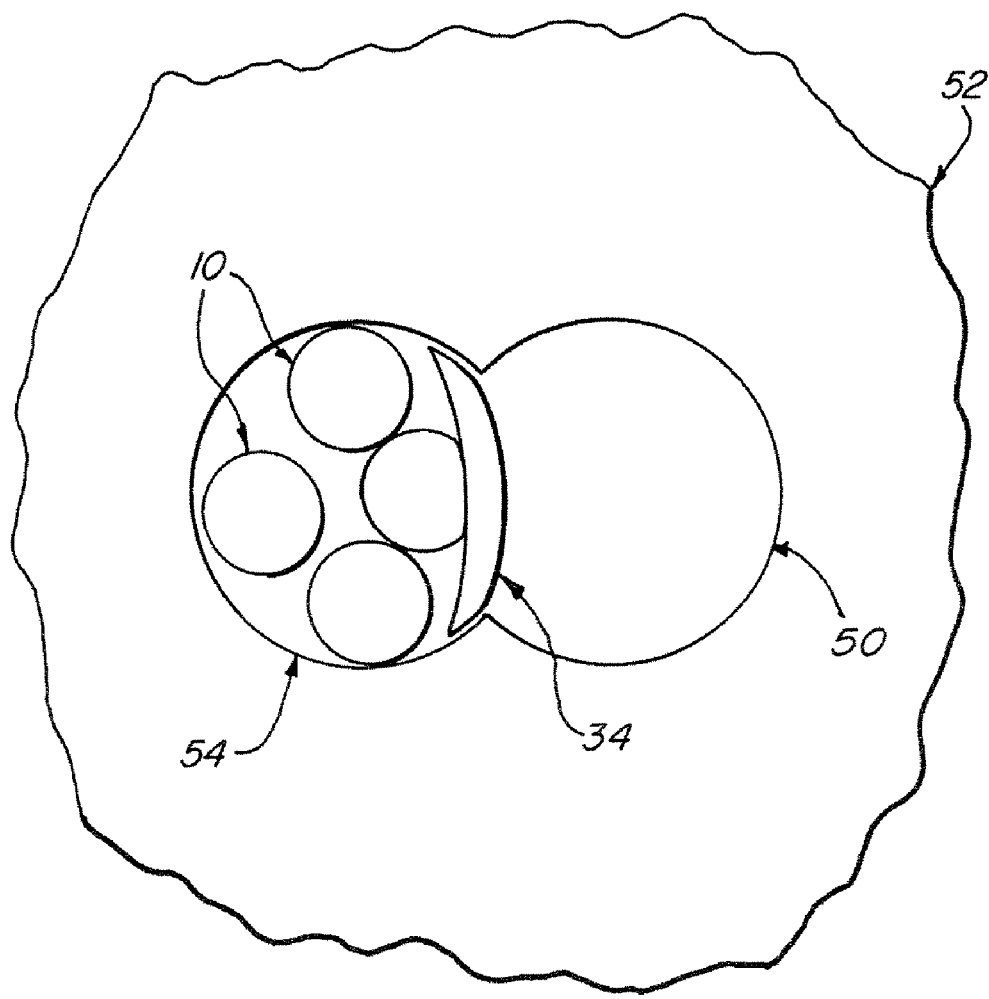
FIG. 18 is a schematic illustration of a peripheral shim used to close off the new bone tunnel hole from the old bone tunnel hole, so as to keep the graft ligament from falling into the old bone tunnel hole.

In some cases, it may be necessary to redo, or "revise", an earlier ACL reconstruction. This frequently involves forming a new bone tunnel hole adjacent to the old bone tunnel hole. If the old bone tunnel hole 50 occupied a less than ideal position in the host bone 52, it is generally desirable to place the new bone tunnel hole 54 in a better position than the old bone tunnel hole. In some circumstances, the new bone tunnel hole will be placed so close to the old bone tunnel hole 50 that the two will actually overlap (FIG. 17). In this case, there may be a danger of a graft ligament strand 10 "falling" out of the new bone tunnel hole and into the old bone tunnel hole, e.g., as shown at 56. With the present invention, a peripheral shim 34 may be used (FIG. 18) so as to close off the new bone tunnel hole 54 from the old bone tunnel hole 50, so as to keep the graft ligament strand from falling into the old bone tunnel hole 50.

It should be appreciated that while the present invention has been discussed above in the context of an ACL reconstruction, it is not intended to be limited to just ACL reconstructions. The present invention will also find application in other sorts of reconstructions, e.g., other types of ligament reconstructions, etc.

What is claimed is:

1. A ligament shim for insertion into a bone tunnel, the ligament shim comprising:
    a body having a first end and a second end, and an axis extending from the first end to the second end;
    the first and second ends being substantially planar;
    the first and second ends having a length and a central width, the length being longer than the central width;
    a first surface and a second surface extending from the first end to the second end and substantially parallel to the axis, at least the first surface being arc-shaped;
    wherein one of the first surface and second surface is adapted to engage a bone tunnel wall and the other surface is adapted to engage a ligament;
    wherein the body comprises a thickness between the first surface and the second surface that is dimensioned such that when one surface engages the bone tunnel wall and the other surface simultaneously engages the ligament, the ligament is forced against a bone tunnel wall; and
    a shim hole extending from the arc-shaped surface to the second surface, the body being otherwise devoid of any further opening.

2. The ligament shim in accordance with claim 1 wherein the first arc-shaped surface extends outwardly from the axis.

3. The ligament shim in accordance with claim 2 wherein the second surface is a flat surface.

4. The ligament shim in accordance with claim 3 wherein the shim hole extends from a crest of the first surface to the second surface.

5. The ligament shim in accordance with claim 1 wherein the first surface and the second surface are arc-shaped and opposed to each other, the first surface extending outwardly from the axis and the second surface extending inwardly toward the axis.

6. The ligament shim in accordance with claim 5 wherein the shim hole extends from a crest of the first surface to a mid-arc portion of the second surface.

7. The ligament shim in accordance with claim 1 further comprising a third surface and a fourth surface, the third surface and the fourth surface both being outwardly rounded and extending from the first end to the second end.

8. A ligament shim for insertion into a bone tunnel, the ligament shim comprising:
    a body having a first end and a second end, and an axis extending from the first end to the second end;
    the first and second ends being substantially planar;
    the first and second ends having a length and a central width, the length being longer than the central width;
    at least a first surface and a second surface extending from the first end to the second end and substantially parallel to the axis;
    wherein the first surface and the second surface are both arc-shaped and are opposed surfaces extending inwardly toward each other adapted to engage ligaments on opposing sides of the body; and
    wherein the body comprises a thickness between the first surface and the second surface that is dimensioned such that when the first surface engages a first ligament and the second surface simultaneously engages a second ligament, both the first and second ligaments are forced against bone tunnel walls; and
    a shim hole extending from the first arc-shaped surface to the second arc-shaped surface, the body being otherwise devoid of any further opening.

9. The ligament shim in accordance with claim 8 further comprising a third surface and a fourth surface, the third surface and the fourth surface both being outwardly rounded and extending from the first end to the second end.

* * * * *